US00PP27350P3

(12) United States Plant Patent
Skelton

(10) Patent No.: US PP27,350 P3
(45) Date of Patent: Nov. 8, 2016

(54) ***ACTINIDIA CHINENSIS* PLANT NAMES 'KZ02'**

(50) Latin Name: *Actinidia chinensis*
Varietal Denomination: KZ02

(71) Applicant: Donald Alfred Skelton, Rangiriri (NZ)

(72) Inventor: Donald Alfred Skelton, Rangiriri (NZ)

(73) Assignee: Kiwi Fruit NZ Limited (NZ)

( * ) Notice: Subject to any disclaimer, the term of this patent is extended or adjusted under 35 U.S.C. 154(b) by 95 days.

(21) Appl. No.: 14/544,977

(22) Filed: Mar. 12, 2015

(65) Prior Publication Data

US 2016/0278254 P1 Sep. 22, 2016

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Actinidia chinensis* cultivar named 'KZ02' is disclosed, characterized by a distinctive yellow inner pericarp and a mid seasonal harvest time. The new variety bears fruit heavily and produces a consistently shaped oblong shaped fruit. The new variety is suitable for commercial production of kiwi fruit.

3 Drawing Sheets

Latin name of the genus and species: *Actinidia chinensis*. Variety denomination: 'KZ02'.

BACKGROUND OF THE INVENTION

The new cultivar is a product of a planned breeding program under the direction of the inventor, Donald Alfred Skelton, a citizen of New Zealand. The seed parent is the unpatented, proprietary seedling variety *Actinidia chinensis* 'A87'. The pollen parent is the unpatented, proprietary seedling variety referred to as *Actinidia chinensis* 'A20'. The crossing was made by the inventor during 1992.

Fruit of the new variety was first evaluated in 1995 with favorable results. After the first evaluation, semi-hardwood cuttings were made of 'KZ02' and were grafted onto seedling rootstocks of *A. deliciosa*. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'KZ02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KZ02' These characteristics in combination distinguish 'KZ02' as a new and distinct *Actinidia chinensis* cultivar:

1. Heavy bearer
2. Consistent fruit shape
3. Medium plant vigor.
4. Precocious
5. Flowering late April, early May 6. Inner pericarp coloration near Yellow 4A

PARENT COMPARISON

The new variety is similar to the seed parent variety in some horticultural characteristics. However, the new variety differs in the following;

1. The new variety has an oblong fruit shape, compared to the ovoid parent fruit.
2. The new variety produces mature fruit during mid-season, compared to late season fruiting of the seed parent.
3. Fruit of the new variety is much larger than that of the seed parent
4. The new variety flowers mid-season, the seed parent flowers early season.

The new variety can be compared to the pollen parent variety, however, the plants clearly differ, as the new variety is a fruit producing female plant and the pollen parent is a non-fruiting male plant. Additionally, the new variety differs in the following;

1. The new variety flowers later than the pollen parent variety.
2. No fruit is produced by the pollen parent.

COMMERCIAL COMPARISON

The new variety is best compared to the commercial variety, 'ZESY002', U.S. Plant Pat. No. 22,355. 'KZ02' is similar to 'ZESY002' in many horticultural characteristics, however, 'KZ02' differs in the following:

1. Ploidy; the new variety is a diploid, 'ZESY002' is a tetraploid.
2. The new variety flowers mid season, this comparator flowers late season.
3. The new variety produces fruit with a brigher yellow (4A) inner pericarp, compared to 8D of this comparator.

The new variety can be compared to the commercial variety 'Y368', U.S. Plant Pat. No. 20,721. 'KZ02' is similar to 'Y368' in many horticultural characteristics, however, 'KZ02' differs in the following:

1. The new variety flowers mid season, this comparator flowers early season.
2. The new variety produces mature fruit mid season, this comparator produces mature fruit early season.

BRIEF DESCRIPTION OF THE PHOTOGRAPHS

The accompanying photograph in FIG. 1 illustrates in full color examples of typical fruits of 'KZ02', while on the plant, as well as typical foliage. This figure illustrates the heavy bearing characteristics of the variety.

Figure 1:
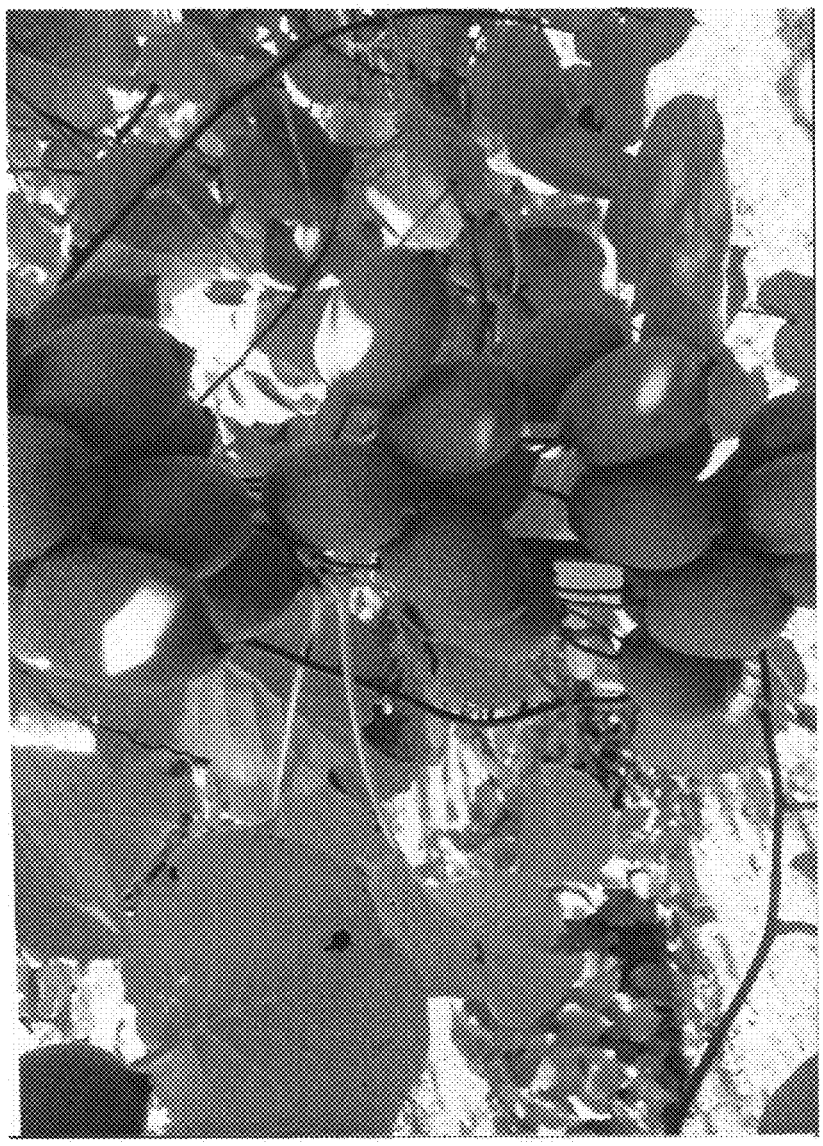
Figure 2:
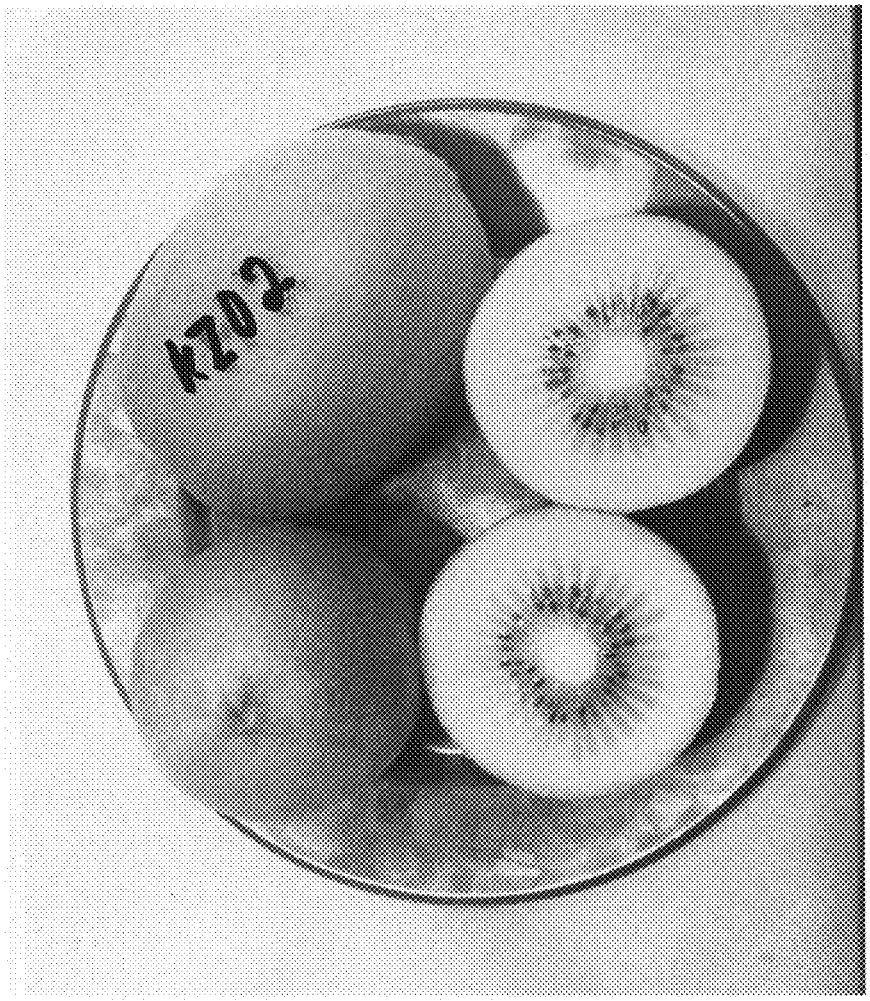
FIG. 2 illustrates fruit harvested from 'KZ02'.
Figure 3:
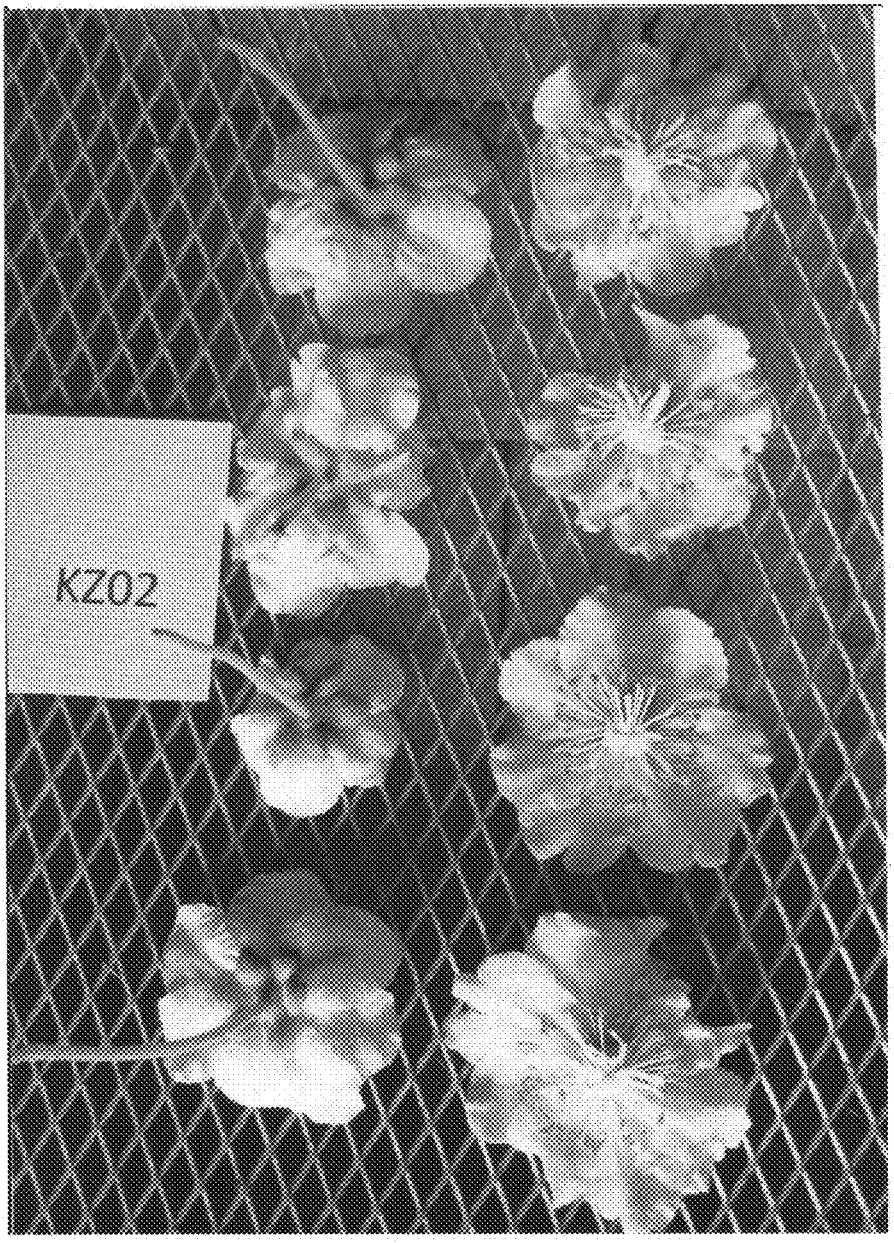
FIG. 3 shows the front and back sides of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KZ02' plants grown outdoors under commercial trial conditions in Rangiriri, New Zealand. The growing temperature ranged from 10° C. to 30° C. during the day and −3° C. to 15° C. at night. Annual rainfall is approximately 125 cm per year. Measurements and numerical values represent an average of 10 typical plant types, measurements of foliage taken from mid June to mid August.

Botanical classification: *Actinidia chinensis* 'KZ02'.

PROPAGATION

'KZ02' can be successfully grafted onto rootstocks of *Actinidia deliciosa.*

PLANT

*Age of the plant described.*—Approximately 9 years.
*Sex expression.*—Female.
*Ploidy.*—Diploid.
*Average height.*—180 cm.
*Average width.*—Canopy is an average of 400 cm by 400 cm. Canopy is pruned to industry standard sizing.
*Vigor.*—Moderate.
*Young shoot color.*—Near RHS Yellow-Green 152D.
*Young shoot texture.*—Glabrous.
*Mature branch/shoot diameter.*—Average 1.5 cm.
*Mature branch/shoot length.*—Average 200 cm.
*Mature branch/shoot texture.*—Rough.
*Stem lenticels description.*—Length: Average 1.0 mm. Width: Average 0.5 mm. Density: Approximately 20 per 5 cm of stem.
*Leaf scar.*—Shallow.
*Trunk diameter.*—Approximately 7.0 cm for a 9 year old vine.
*Trunk texture.*—Rough.
*Trunk color.*—Near RHS Greyed-Green 198A.

FOLIAGE

Leaf:
*Average length.*—Average range from 12.8 cm to 17.5 cm.
*Average width.*—Average range from 15.1 cm to 19.0 cm.
*Shape of blade.*—Reniform.
*Apex.*—Obtuse.
*Base.*—Cordate.
*Attachment.*—Petioled.
*Margin.*—Entire.
*Texture of top surface.*—Glabrous, rugose.
*Texture of under side.*—Downy pubescence.
*Color.*—Mature foliage upper side: Near RHS Green 141 C. Mature foliage under side: Near RHS Green 138C.
*Petiole.*—Length: Average range from 5.5 cm to 9.0 cm. Diameter: Approximately 0.6 cm. Texture: Glabrous. Color: Near RHS Red 49B.

FLOWER

*Flowers per inflorescence.*—1.
*Bud color.*—Near RHS White 155C.
*Bud shape.*—Spherical.
*Bud break.*—August 20 (Rangiriri, New Zealand).
*First flower.*—October 10.
*Diameter.*—Average 5.5 cm.
*Depth.*—Average 5 cm.
*Petal quantity.*—Average 8 per flower.
*Petals overlapping.*—Yes.

Petals:
*Length.*—Approximately 2.5 cm.
*Width.*—Approximately 2.6 cm.
*Shape.*—Spatulate.
*Aspect.*—Slightly undulating.
*Margin.*—Entire, with infrequent irregular shallow crenations.
*Texture.*—Glabrous, all surfaces.
*Base.*—Attenuate.
*Apex.*—Obtuse.
*Petals color.*—Upper surface: Near RHS White 155B. Lower surface: Near RHS White 155C.
*Filament color.*—Near RHS White N155A.
*Anther color.*—Near RHS Greyed-Orange 165A.
*Attitude of styles.*—Upright.
*Style color.*—Near RHS White 155C.
*Style quantity.*—1.
*Hair on ovary.*—Moderately dense, White 155A.
*Color of ovary.*—Near RHS White 155A.
*Number of sepals.*—7 to 8.
*Color of sepals.*—Near RHS Green 144C upper and lower surfaces.
*Sepal width.*—Approximately 0.5 cm.
*Sepal length.*—Approximately 0.8 cm.
*Sepal texture.*—Velvety.
*Sepal shape.*—Ovate.
*Sepal margin.*—Entire.
*Sepal apex.*—Acute.
*Sepal base.*—Rounded.

Peduncle:
*Length.*—Average 1.7 cm.
*Diameter.*—Average 0.1 cm.

*Color*.—Near RHS Yellow-Green 144C.
*Texture*.—Smooth.

FRUIT

*Average weight*.—110 grams.
*Minimum weight*.—85 grams.
*Maximum weight*.—140 grams.
*Average length*.—7.6 cm.
*Average diameter*.—4.3 cm.
*Color outer pericarp*.—Near RHS Yellow 4A.
*Color inner pericarp*.—Near RHS Yellow 4C.
*Core color*.—Near RHS White 155A.
*Core diameter*.—Average 1.6 cm.
*General shape*.—Oblong.
*Brix at consumption*.—18.5.
*Brix at harvest*.—7.5.
*Fruit peduncle length*.—1.7 cm.
*Fruit peduncle width*.—1 mm.
*Median cross section*.—Circular.
*Stylar end shape*.—Slightly blunt protruding.
*Shoulder shape*.—Square.
*Calyx ring*.—Yes.
*Calyx ring expression*.—Weak.
*Skin color at harvest*.—Near RHS Greyed-Yellow 162D.
*Hair on fruit skin*.—Downy.
*Hair adherence to skin*.—Light.
*Skin adherence to flesh at maturity*.—Firm.
*Fruit core shape*.—Round.
*Core-woody spike*.—No.
*Lenticels on fruit*.—Not observed, minute or obscured by downy pubescence.
*Mature seed color*.—Near Black 202A.
*Harvest time*.—Late April(Southern Hemisphere, Rangiriri, New Zealand).
*Overall cropping quantity*.—100 tons per hectare.

Fruit stem:
*Length*.—Average 1.7 cm.
*Diameter*.—Average 1 mm.
*Color*.—Near RHS Yellow-Green 144C.
*Texture*.—Smooth.

OTHER CHARACTERISTICS

Storage life: Storage life is a minimum of 100 days at 2° C.
Disease/pest resistance: Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'KZ02' as herein illustrated and described.

* * * * *